United States Patent [19]

Oberg et al.

[11] Patent Number: 5,396,893
[45] Date of Patent: Mar. 14, 1995

[54] METHOD AND APPARATUS FOR ANALYZING HEART AND RESPIRATORY FREQUENCIES PHOTOPLETHYSMOGRAPHICALLY

[76] Inventors: Ake P. Oberg, Ugglebovägen 79, S-590 60 Ljungsbro; Lars-Göran Lindberg, Knektgatan 18, S-582 65 Linköping, both of Sweden

[21] Appl. No.: 920,274
[22] PCT Filed: Feb. 14, 1991
[86] PCT No.: PCT/SE91/00106
 § 371 Date: Aug. 3, 1992
 § 102(e) Date: Aug. 3, 1992
[87] PCT Pub. No.: WO91/11956
 PCT Pub. Date: Aug. 22, 1991

[30] Foreign Application Priority Data

Feb. 16, 1990 [SE] Sweden .................. 9000564

[51] Int. Cl.$^6$ ........................... A61B 5/0205
[52] U.S. Cl. ..................... 128/671; 128/687; 128/666
[58] Field of Search ............. 128/633, 664–667, 128/670–671, 668, 687–690

[56] References Cited

U.S. PATENT DOCUMENTS

| | | |
|---|---|---|
| 4,183,360 | 1/1980 | Carlson et al. |
| 4,379,460 | 4/1983 | Judell .................. 128/671 |
| 4,781,201 | 11/1988 | Wright et al. ........... 128/671 |
| 4,788,982 | 12/1988 | Gedeon et al. |
| 4,934,372 | 6/1990 | Corenman et al. ........ 128/666 X |
| 5,078,136 | 1/1992 | Stone et al. ........... 128/666 X |

FOREIGN PATENT DOCUMENTS

| | | |
|---|---|---|
| 0109826 | 5/1984 | European Pat. Off. |
| 319158 | 6/1989 | European Pat. Off. |
| 0341327 | 11/1989 | European Pat. Off. |
| 0349755 | 1/1990 | European Pat. Off. |
| 0335357 | 9/1990 | European Pat. Off. |
| 3811689 | 6/1989 | Germany . |
| 03211 | 8/1985 | WIPO . |

*Primary Examiner*—Angela D. Sykes
*Attorney, Agent, or Firm*—Sughrue, Mion, Zinn, Macpeak & Seas

[57] ABSTRACT

A pulse-frequency analyzing monitor which is provided with an optical sensor and which is intended for measuring photoplethysmographically the blood circulation of a subject, such as a body part of a human being or an animal, includes a light source, preferably a light-emitting diode for infrared light, fibre optics, a detector unit for detecting the alternating voltage, or AC-component of a generated PPG-signal for the purpose of determining the heart frequency of the subject, an electronic amplifying unit and a presentation unit, for instance an oscilloscope of a display unit. The apparatus also includes means for separating from the detected PPG-signal a signal component which indicates the respiration frequency of the subject. The PPG-signal is coupled to a filter, preferably a digital filter, which enables limit frequencies and the degree of amplification to be set. The digital filter may be a component of a microprocessor which is able to eliminate disturbances, for instance disturbances emanating from 50 Hz stray light, in addition to separating signals concerning the heart and respiration frequency of the subject. The invention also relates to a method of carrying out such photoplethysomographic measuring processes.

11 Claims, 4 Drawing Sheets

METHOD AND APPARATUS FOR ANALYZING HEART AND RESPIRATORY FREQUENCIES PHOTOPLETHYSMOGRAPHICALLY

TECHNICAL FIELD

The present invention relates to monitoring apparatus provided with an optical sensor and functioning to analyze pulse frequencies by measuring the blood circulation of a measuring object, such as a part of the human body or an animal body using photoplethysmography (PPG-measuring), said apparatus being of the kind set forth in the preamble of claim 1. The invention also relates to a method of taking such measurements.

Photoplethysmography (hereinafter abbreviated to PPG) has been known to the art for more than 50 years and is applied technically for measuring peripheral blood circulation. The method is primarily used for measuring heart frequencies and blood circulation when performing surgery. The method has many advantages, since, among other things, it is non-invasive and does not subject the patient to any appreciable trauma. Furthermore, the method requires no highly expensive or complicated equipment in order to be put into effect.

When light from a suitable light source impinges on the skin, the light is dampened or attenuated according to the nature of the tissue on which the light impinges. This light attenuation is assumed to be constant. The light also passes through a number of blood vessels and is also attenuated by the blood present. The light is attenuated as a result of a number of complex processes, such as absorption, reflection and different forms of scattering. The PPG-technique is based on the assumption that the more blood that is present in the volume investigated, the more the light is attenuated. This results in two signal components of interest, namely a DC-component which corresponds to the total amount of blood in the investigated volume and an AC-component which signifies pulsation of the blood flow.

In order to study the aforedescribed phenomenon, it is necessary to use a light source, a light detector, amplifying electronics and a display unit, for instance an oscilloscope or a printer.

The light source and the detector may be placed on a respective side of the object on which blood circulation is to be measured, and the detector consequently measures the light transmitted. This technique is, at times, referred to as transmission-photoplethysmography and can only be applied to a few skin surfaces, such as fingers, ear lobes and toes.

A more general method is to place both the light source and the detector in one and the same probe and measure the light reflected. This technique is known as reflection * and is the dominating technique. It has long been understood that the pulsating component or AC-component of the PPG-signal is contingent on changes in blood volume during each heart beat. The greater the volume of blood, the less light will impinge on the detector.

It is obvious, however, that this is not the whole truth. Tests have been carried out in which blood has been allowed to pulsate in rigid glass tubes, where changes in volume are impossible and where solely the flow rate pulsates. A pulsating PPG-signal is also obtained in this case, which can be explained by the detection of changes in orientation of the erythrocytes, which varies during each heart beat.

In summary, there are at least two reasons for the AC-component, namely a change in blood volume and the orientation of the erythrocytes.

A typical PPG-signal has, in the time plane, the form of a blood-pressure curve having the same periodicity as the heart beats. The signal also includes a number of low frequencies.

The present invention is based on the realization that the lower frequencies occur as a result of changes in blood flow caused by the sympathetic nerve system and by respiration, this realization being based on the known fact that the intrathoracic pressure is lowered when breathing-in, or inspiring. This subpressure is utilized to "suck" the venous blood into the atrium and ventricle.

The invention departs from this starting point and assumes that this subpressure causes variations in blood flow in venous plexus and also that it should be possible to detect this variation with the aid of the PPG-technique, particularly by using a technique which enables measurements to be made in the venous plexus.

Nerve signals in the sympathetic nerve system also influence the blood flow. The smooth muscle around the vessels pulsates at a frequency which lies close to the respiration frequency. This pulsation is normally referred to as Traube-Hering's waves, after the scientists' Traube-Hering. Waves of a still lower frequency are also found, these waves normally being referred to as Mayer's waves.

The blood also pulsates through the so-called arteriovenous anastomises, so as to control body temperature. This normally occurs at a frequency of about 0.3 Hz and is designated Burton waves.

DISCLOSURE OF THE INVENTION

The present invention is based on the aforesaid realization and on measurements, or assays, carried out with the aid of apparatus that has been constructed in accordance with the theory on which the present invention is based.

The inventive monitoring apparatus intended for measuring blood circulation is of the kind set forth in the preamble of claim 1 and has the characterizing features set forth in the characterizing clause of said claim.

The exhaustive experimentation, which forms the basis of the invention and which is briefly described herebelow, has shown that respiration is the totally dominating low-frequency component of the PPG-signal.

It was found from the series of experiments performed that the extracted signal can be encountered substantially irrespective of where in the body the probe is placed. This leads to the conclusion that the extracted PPG-signal constitutes a measurement of variations in blood pressure caused by respiration, and therewith also variations in the flow of blood through the object under examination.

It is expected that the inventive monitoring apparatus will find universal use within human care establishments. In the case of patients in intensive care wards or under anaesthetic or under postoperative conditions, it is important to monitor heart and respiration frequencies. When these two physiological variables are known, the doctor or nursing syster will have a good picture of the patient's general condition. Monitoring of these variables under anaesthetic conditions can facilitate the assessment of the depth of anaesthesia.

Above all, the invention avoids those serious disadvantages that are associated with respiratory frequency monitoring methods and apparatus hitherto used, all of which are normally unreliable, besides being both strenuous and complex.

It is generally more important to monitor respiration parameters in the case of infant care than in the case of adults under intensive care. In this regard, the inventive monitoring apparatus is superior to the technique which has been used most frequently hitherto, namely the use of impedance plethysmography with the aid of ECG-electrodes placed on the surface of the skin, among other things because such electrodes (normally three) take-up a relatively large area of the thorax. When requiring to make X-ray examinations, it is necessary to remove the electrodes, since they are not transparent to X-rays.

Furthermore, light disturbances from peripheral electrical apparatus are induced in ECG-cables with associated input amplifiers. The signal cables are coupled both inductively and capacitively. When carying out surgery, it is impossible to carry out ECG-recordings and to measure heart frequencies over prolonged periods of time, due to the surgical application of diathermy.

ECG-electrodes and the paste used together therewith cause irritation of the skin, particularly when monitoring is effected over a prolonged period and particularly in the case of infants whose skin is very tender and sensitive. The electrodes and associated leads or cables also limit the ability of the child to move.

The present invention provides important direct advantages in relation to the aforesaid, and also affords indirect advantages with respect to methods of measuring respiration frequency.

For example, the inventive monitoring apparatus can be applied and handled with ease; it avoids the aforesaid problems associated with prolonged use of skin electrodes; it is free from disturbances during surgery in which diathermy is applied; and affords a wide degree of freedom with regard to positioning of the sensor. For example, a sensor-provided probe can be placed on a finger or on a toe, at a distance from the thorax region where another investigation is being made. Furthermore, the sensor element can be made very small, such as not to interfere with X-ray examinations to any appreciable extent.

An additional, very important advantage afforded by the inventive monitoring apparatus is that it can be integrated with a number of different medical instruments of the kind where heart frequency and respiration frequency are important parameters, for instance pulsoxymetry and defibrillators.

In order to enable measurements to be taken directly on patients, it is necessary to equip the monitoring apparatus with one or more filters. This will result, however, in difficulty in selecting limit frequencies, since the signal can exhibit pronounced variations.

Accordingly, one preferred embodiment of the invention is characterized in that the apparatus includes one or more filters, preferably digital filters, which have means for setting limit frequencies and the degree of amplification. Filters of this kind are suitably incorporated in the apparatus, which will also preferably include means for electronically detecting the frequency content of the signal for selection and setting of limit frequencies.

According to another embodiment of the monitoring apparatus, the filters are adaptive and are constructed to adapt to the prevailing heart and/or respiration frequency, so as to optimize the filter properties.

Furthermore, the monitoring apparatus will preferably be provided with means for DC-compensating the PPG-signal, so as to balance-out the low frequency components of said signal automatically, without experiencing harmful energy losses.

In the case of one embodiment of the invention which is particularly beneficial in practical application, the monitoring apparatus includes a probe which is intended to be placed on a suitable part of the body, for example a finger, and which includes means for delivering light to said body part and means for capturing light which passes through said body part or which is reflected therein, for the purpose of passing this light to the detector unit. This monitoring apparatus is characterized by optical fibres connected to the probe and functioning to conduct light from a light source to the skin and from the skin to the detector unit respectively.

By conducting, in said apparatus, the light through optical fibres to and from the skin, there is obtained a system which is highly resistant to electromagnetic disturbances or interference, a feature which is extremely important within the sphere of medical treatment. This particular feature enables the heart frequency and respiration frequency to be recorded during surgery in which diathermy is applied. An apparatus of this kind which is insensitive to disturbances during surgery represents a very important step forwards in the art.

The inventive monitoring apparatus preferably includes a microprocessor which is programmed to calculate the Fourier transform, and/or to separate signals concerning the heart and respiration frequencies of the object by digital filtration, and/or to eliminate disturbances, emanating, for example, from stray light of frequency 50 Hz.

A further possibility afforded by the use of microprocessor technology is that of combining the measuring process with SaO2-measuring with pulsoxymetry.

The present invention also relates to a method of carrying out photoplethysmographic measuring processes, this method being characterized mainly by the characteristic features set forth in claim 9.

DISCLOSURE OF THE EXPERIMENTS PERFORMED

With the intention of confirming the aforedescribed theory scientifically, namely the theory that it is also possible to separate from a PPG-signal whose dominating component forms a measurement of the heart frequency of the object being examined, a signal component which discloses the respiration frequency of said object, a simple photoplethysmograph was constructed. Four different measuring probes were mounted on the photoplethysmograph, all of which probes used a light-emitting diode as a light source. One probe utilized the wavelength 875 nm, two utilized the wavelength 940 nm and one utilized the wavelength 950 nm. All probes measured reflected light. The photoplethysmograph operated either within the frequency range of 0.2–10 Hz or the frequency range 0.2–20 Hz.

The photoplethysmograph was used to measure the blood circulation of dogs, cats, adult males aged 35 years and infants in incubators. In order to show both the respiration frequency and heart frequency in the photoplethysmograph signal, the heart frequency and respiration frequency of the adults and the infants were recorded separately with the aid of other methods. In the case of the animals used in this experiment, solely the respiration frequency was recorded separately. These measurements were used as reference signals in the measuring-data analysis. All measurements were recorded on a measurement tape-recorder.

The measurement data was analyzed partly in the time plane, where the two components in the photoplethysmograph signal were filtered out, and partly in the frequency plane, wherein the power spectrum was calculated?. A cross-correlation function for the photoplethysmograph signal and the reference signals was also calculated. The following conclusions can be drawn from these analyses:

The apparatus functions well on adults. The heart frequency and respiration frequency can be separated by means of filter techniques. The heart frequency is the dominant signal component. The two components are clearly evident in the power spectrum and the cross-correlation function shows correlation with the reference signals.

In the case of infants in respirators, respiration is the totally dominant component. It is slightly more difficult to filter-out the two components in the case of infants than in the case of adults. Although the two frequencies are evident in the power spectrum, respiration dominates the spectrum totally. The cross-correlation function shows correlation with the reference signals.

The respiration frequency is the dominant signal component in the case of animals. Although a high frequency component can be filtered-out, it cannot be guaranteed that this component is the heart frequency. The power spectrum has a broad band with many peaks or spikes whose origin cannot readily be established. The cross-correlation function was constructed solely for respiration, where correlation can be shown.

BRIEF DESCRIPTION OF THE DRAWINGS

A more detailed account of the experiments carried out is given below, with reference to the accompany drawings, in which.

DETAILED DESCRIPTION OF THE DRAWINGS

Infrared light-emitting diodes were used as the light source. Light-emitting diodes are small, mechanically insensitive and have a light intensity which is proportional to the diode current. The AC-component of the PPG-signal is weak and must be greatly amplified. The light intensity should be high, in order to obtain a high signal level. This is achieved by pulsating the light-emitting diode with a high current. This enables a much higher diode current to be used than in the case of continuous light. The use of pulsated light results in time-discrete measurement of a time-continuous signal.

According to the sampling theorem, it is necessary for the pulse frequency to be twice as large as the frequency content of the signal, in order to recreate the continuous signal. This frequency content should be beneath 20 Hz. The pulse frequency selected was 1 kHz, which fulfils the sampling theorem more than well. The diode illuminating time was 40 $\mu$s, which constitutes a fraction of the period time 1 ms. Since the illuminating time is so short in relation to the dark time, it is possible to use a very high diode current without destroying the light-emitting diode.

For the purpose of obtaining a continuous measurement response, the measuring values are maintained constant between each new measuring process, with the aid of a sample-and-hold circuit. In order to guarantee that a measurement value is obtained when the diode emits light at full intensity, the sample-and-hold circuit is closed (and therewith holds the measurement value) before extinguishing the light-emitting diode.

The signal from the sample-and-hold circuit is equalized by passing said signal through a low-pass filter.

Figure 1:
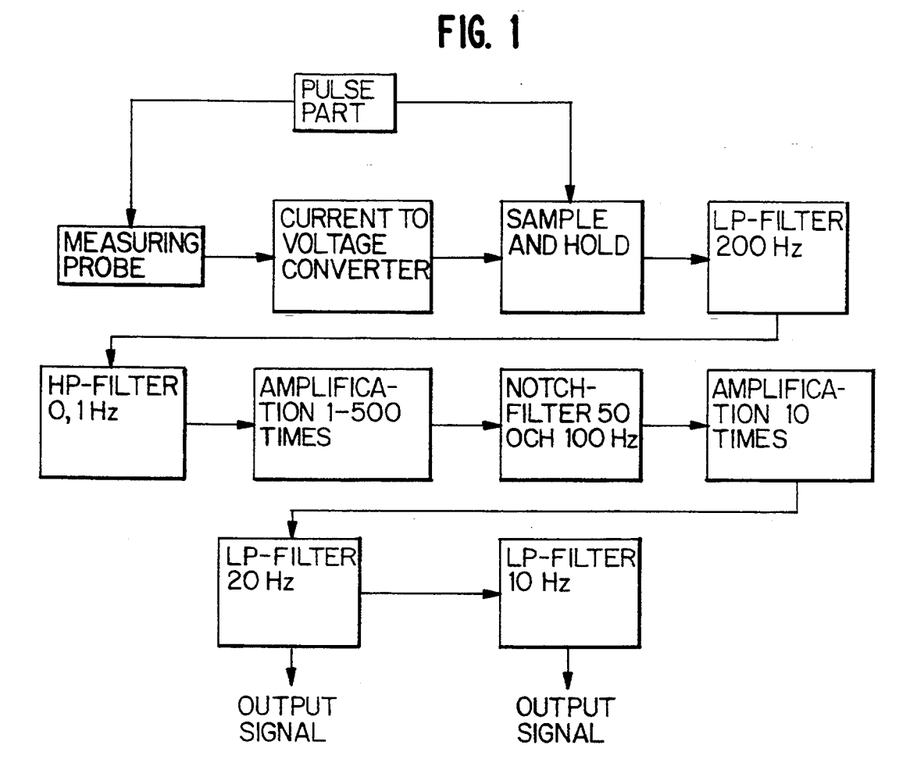
FIG. 1 is a block schematic which illustrates the principle construction of the measuring electronics used.

The principle construction of the measuring electronics will be seen from FIG. 1. References are made to the circuit diagram shown in FIG. 4.

The Measuring Probe

Four different measuring probes, referenced A–D, were constructed during the experimental period. All of these measuring probes included a detector in the form of a light-emitting diode model S-4C from United Detector Technology.

Three different light-emitting diodes were used, namely:

| Probe | | Wavelength | Light Power |
|---|---|---|---|
| A | Philips CQY 58 | 875 nm | 0.5 mW |
| B, C | Telefunken TSUS 5400 (corresponds to Philips CQY 99) | 950 nm | 15 mw |
| D | Hewlett-Packard HEMT 1001 | 940 nm | 2.5 mW |

It should be observed in this respect that the light was comparitively broad-band light and that the wavelength values refer to maximum intensity. The power value denotes the power radiated totally in a hemisphere and is estimated from existing data sheets in the case of HEMT 1001. It should also be mentioned that the light-emitting diodes spread light differently.

Figure 2:
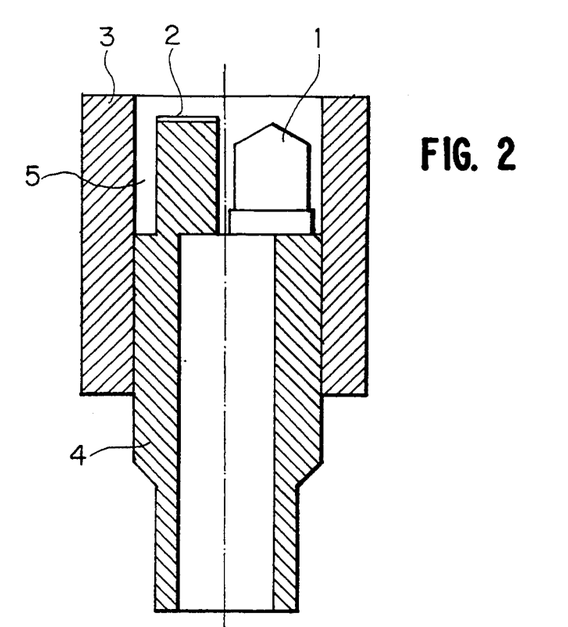
FIGS. 2 and 3 are schematic views of measuring probes used in the experiment series.
Figure 2A:
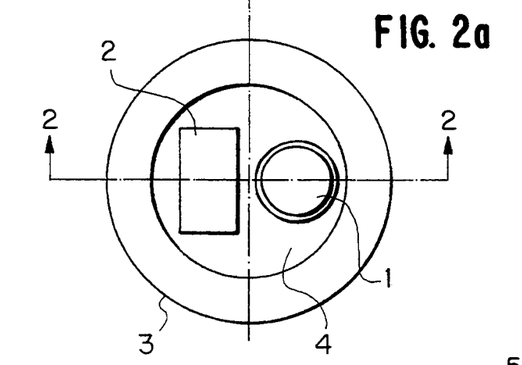

FIGS. 2 and 2a illustrate a measuring probe comprising an acrylic tube 4 in which a light-emitting diode 1 and a detector in the form of a light-emitting diode 2 are embodied or cast with epoxy resin 5. The tube 4 has a diameter of 8 mm and is surrounded by a tube 3 of diameter 12 mm.

Figure 3:
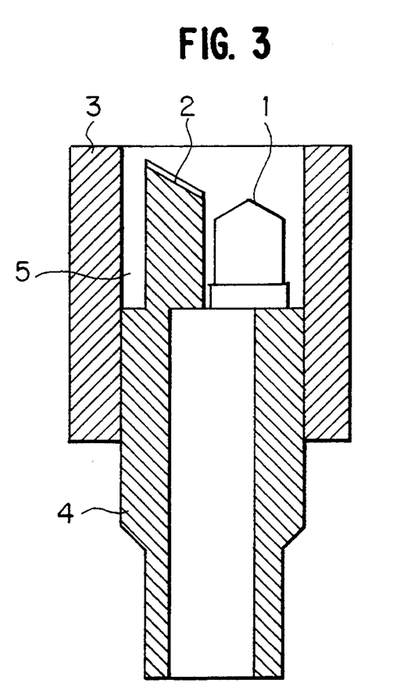

The probe illustrated in FIG. 3 differs from the probe illustrated in FIG. 2, in that the detector 2 is angled in relation to the detector surface.

The following light-emitting diodes were used with the different probes:

Probe A uses light-emitting diode CQy 58

Probes B and C uses light-emitting diode HEMT 1001

Probe D uses light-emitting diode TSUS 5400

Probes A and D were constructed in the same way as the probe B shown in FIG. 2.

The cables used between probes and electronic devices were very thin and flexible, screened four-conductor cables sold by Telko under the trade name Pickuptråd PU 402.

Figure 4:
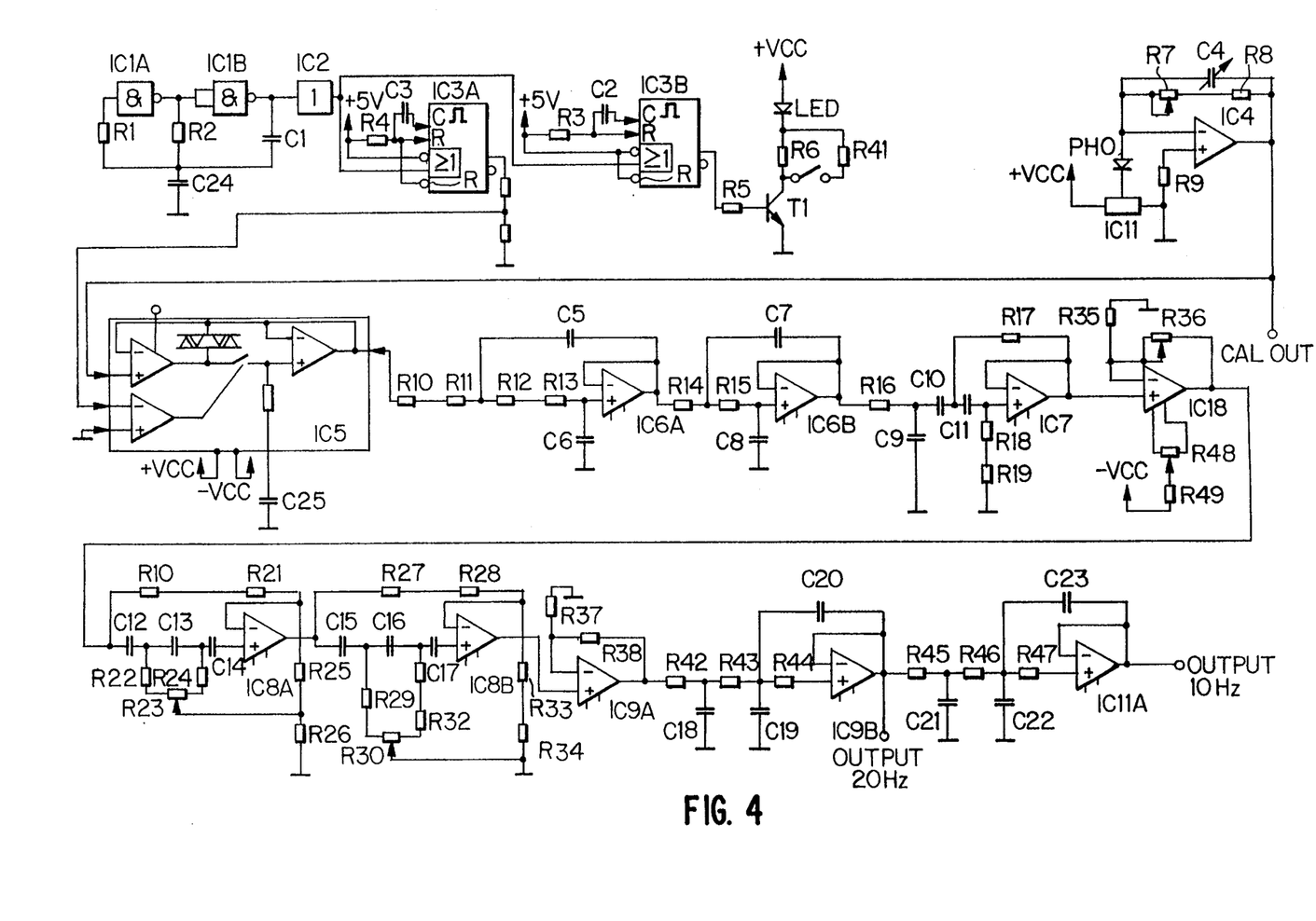
FIGS. 4 and 5 are circuit diagrams.
Figure 5:
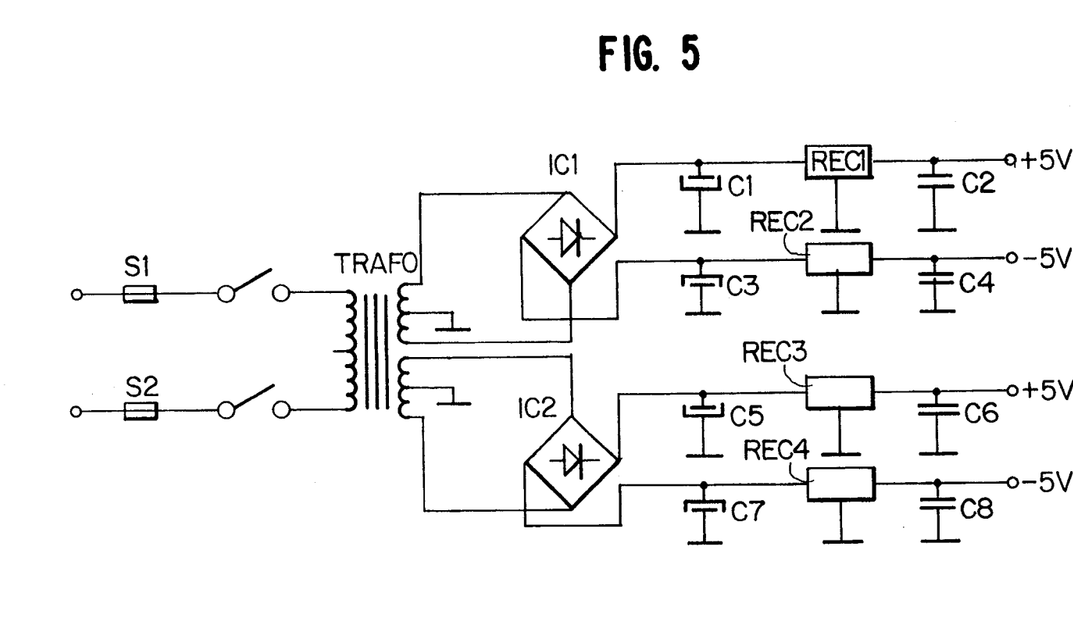

FIGS. 4 and 5 are circuit diagrams of embodiments of the pulse electronics circuity employed in the present invention. Exemplary values for the components used in these embodiments are set forth in Tables 1 and 2 as follows:

TABLE 1

| component | value or type | component | value or type |
|---|---|---|---|
| IC1 | 4011 | R1 | 10M |
| IC2 | 4050 | R2 | 15k |
| IC3 | 4538 | R3 | 3.9k |
| IC4 | TL071 | R4 | 3.3k |
| IC5 | NE537 | R5 | 22k |
| IC6 | TL072 | R6 | 18Ω |
| IC7 | TL071 | R7 | 0-100k |
| IC8 | TL072 | R8 | 1k |
| IC9 | TL072 | R9 | 27k |
| IC10 | TL071 | R10 | 2.2k |
| IC11 | AD580 | R11 | 39k |
|  |  | R12 | 39k |
| T1 | BD667A | R13 | 2.2k |
|  |  | R14 | 39k |
| PHO | UDT S-4C | R15 | 39k |
|  |  | R16 | 100Ω |
| LED | probe A:CQY 58 | R17 | 1.8M |
|  | probe B:HEMT 1001 | R18 | 3.9M |
|  | probe C:HEMT 1001 | R19 | 1.5M |
|  | probe D:CQY 99 | R20 | 480k |
|  |  | R21 | 150k |
| C1 | 22 nF | R22 | 4.7k |
| C2 | 10 nF | R23 | 0-100k |
| C3 | 10 nF | R24 | 75k |
| C4 | 0-40 pF | R25 | 82Ω |
| C5 | 33 nF | R26 | 2.7k |
| C6 | 15 n | R27 | 480k |
| C7 | 0.22 μF | R28 | 150k |
| C8 | 6.8 nF | R29 | 4.7k |
| C9 | 10 μF | R30 | 0-50k |
| C10 | 0.22 μF | R31 | 92k |
| C11 | 0.22 μF | R32 | 33k |
| C12 | 47 nF | R33 | 68Ω |
| C13 | 47 nF | R34 | 2.2k |
| C14 | 47 nF | R35 | 1k |
| C15 | 22 nF | R36 | 0-500k |
| C16 | 22 nF | R37 | 1k |
| C17 | 22 nF | R38 | 10k |
| C18 | 22 nF | R39 | 8.2k |
| C19 | 1 nF | R40 | 8.2k |
| C20 | 0.1 μF | R41 | 18Ω |
| C21 | 22 nF | R42 | 560k |
| C22 | 1 nF | R43 | 560k |
| C23 | 0.1 μF | R44 | 560k |
| C24 | 15 nF | R45 | 1M |
| C25 | 1.0 μF | R46 | 1M |
|  |  | R47 | 1M |
|  |  | R48 | 0-100k |
|  |  | R49 | 1.5k |

The digital IC-circuits are supplied with a voltage +Vcc of +5 V whereas the OP-amplifiers are supplied with +Vcc and a voltage −Vcc of −5 V. Also, each of the digital circuits are provided with a switch-off capacitor of 0.1 μF between °Vcc and ground. The OP amplifiers have similar switch-off capacitors between +Vcc and ground as well as between −Vcc and ground.

TABLE 2

| component | value or type | component | value or type |
|---|---|---|---|
| Trafo | Tradania type TD3701 |  |  |
| S1 | 50 mA | S2 | 50 mA |
| IC1 | PBDF104 | IC2 | PBDF104 |
| C1 | 1000 μF | C2 | 0.1 μF |
| C3 | 1000 μF | C4 | 0.33 μF |
| C5 | 1000 μF | C6 | 0.1 μF |
| C7 | 1000 μF | C8 | 0.33 μF |
| REG1 | 7805 | REG2 | 79L05 |
| REG3 | 78L05 | REG4 | 79L05 |

Pulse Electronics

The pulse electronics used had two functions, firstly to drive the light-emitting diodes and secondly to generate and deliver control signals to the sample-and-hold circuit. The fundamental component of the pulse electronics is a bistable flip-flop which generates a square wave having a frequency of 1 kHz. This flip-flop is constructed around two Nand-gates (IC 1A and B in the circuit diagram of FIG. 4), and a buffer circuit (IC 2). The clock frequency is proportional to the product R2 and C1. The capacitor C24 is required, to lead away disturbing high frequencies.

The control pulses are generated by a monostable flip-flop (IC3), which is triggered on positive flanks by flanks of the square wave.

Those times at which the monostable flip-flop is "high" is determined by the product R3 and C2 for the light-emitting diode, and by the product R4 and C3 for the sample-and-hold circuit.

Current is supplied to the light-emitting diode through a transistor stage built around a Darlington transistor (T1 in FIG. 4). A Darlington transistor is actually two transistors connected in series and has the positive property of having a very high current-amplifying factor.

The voltage drop across collector and emitter reached about 1.4 V.

The light-emitting diode control pulse was connected to the base of the transistor via a resistor (R5), which was dimensioned so that the transistor would bottom at high pulse values and throttle at low pulse values.

The resistor R41 was coupled in parallel with the collector resistor R6 by means of a switch on the front panel of the apparatus used, such as to obtain a high collector current and a high light intensity. The collector current was 130 mA in position "low" and 180 mA in position "high".

The Current-Voltage Converter

The light-emitting diode in the measuring probe was biased electrically with +2.5 V in the reverse direction. This voltage was produced by IC11, which is a precision regulator and which held the voltage stable. A linear detector response was guaranteed in this way. The light-emitting diode now delivered a reverse current which was proportional to the detected light intensity. This current was converted to a voltage, by a current-voltage converter constructed around an operational amplifier (IC4).

It shall be noted that the current-voltage converter was an inverting circuit.

The Sample-and-Hold Circuit (IC5)

The circuit functioned to hold the time-discrete measurement values constant between each new measuring process. Sample-and-hold circuits, however, are encumbered with the disadvantage that disturbances in the form of spikes from the control logic leak through to the measurement value. This is particularly pronounced in respect of the weak AC-component. In order to reduce this disturbance, the amplitude of the control signal was scaled down to about 2 V over the resistors R39 and R40. An external holding capacitor C15 on 1.0 82 F was connected to the circuit. This capacitor also assisted in damping the disturbance spikes.

Low-Pass Filter 200 Hz

The purpose of the first low-pass filter was to eliminate the disturbance spikes deriving from the sample-and-hold circuit. The filter was an active Tjebychev filter of the fourth order, followed by a passive RC-link. The filter had been designed to permit 0.5 dB ripple in the pass band and to have a cut-off frequency of 200 Hz. The filter was built-up around two cascade-coupled operational amplifiers (IC 6A and B) and the RC-link R16 and C9.

The High-Pass Filter 0.1 Hz

The high-pass filter eliminated the DC-component, thereby enabling amplification of the AC-component. The filter was an active Tjebychev filter of the second order, constructed around an operational amplifier (IC7). The filter was designed to permit 0.5 dB ripple in the pass band and to have a cut-off frequency of 0.1 Hz.

Amplification 1–500 Times

The amplifier was a non-inverting amplifier constructed around a offset-compensated operational amplifier (IC10). The amplification was varied with the aid of a potentiometer positioned on the front panel.

Notch Filter 50 and 100 Hz

The weak AC-component was greatly disturbed by the net frequency 50 Hz, and also by disturbances from lamps and fluorescent tubes at 100 Hz. These disturbances were eliminated in two cascade-coupled notch filters. The notch filters were constructed around two operational amplifiers (IC 8A for 50 Hz and IC 8B for 100 Hz). The filters could be adjusted in the frequency direction?, with the aid of potentiometers R29 for the 50 Hz-filter and R30 for the 100 Hz-filter, such as to filter-off precisely the desired frequency.

Amplification 10 Times

The signal was amplified a further 10 times in a non-inverting amplifier constructed around an operational amplifier (IC9A).

Low-Pass Filter 20 Hz

The signal passed through an active Tjebychev filter of the third order, having a cut-off frequency of 20 Hz. This construction permitted a 0.3 dB ripple in the pass band. The filter was constructed around an operational amplifier (IC9B). The output signal was coupled to a BNC-switch labelled "Output 20 Hz" located on the front panel.

Low-Pass Filter 10 Hz

The signal finally passed through a low-pass filter of the same kind as that described in the aforegoing, with the cut-off frequency of 10 Hz. The signal was then coupled to a BNC-switch labelled "Output 10 Hz" located on the front panel.

The Net Part

The measuring electronics comprised a digital pulse part, and an analogue amplifying and filtering part. One problem which readily occurs when mixing digital technique with analogue technique is that disturbances occur in the form of spikes from the digital side to the analogue side. This disturbance can be reduced by using a separate supply voltage on the two parts. Accordingly, the built-in power unit was constructed around a transformer which had two secondary windings, each producing a secondary voltage of 12 V. This alternating voltage was rectified to ±5 V with the aid of rectifying bridges, smoothing and disturbance-eliminating capacitors and integrated regulators. Particular mention can be made to the fact that the light-emitting diode of the probe was powered by a current of between 100 and 200 mA. Consequently, there was used a more powerful regulator capable of delivering more current to the digital ±5 V-side (cf the circuit diagram shown in FIG. 5).

The Light Intensity of the Probes

The following measuring process was carried out in order to obtain an estimation of the mutual intensity relationship between the various probes.

The probes were connected and a photometer was held directly against the probes. The luminous intensity of the probes was observed from the photometer. It shall be noted that this is an integrated measurement value and not the intensity when the diodes are illuminated. The measurement values are shown in the following table.

| Probe | Intensity "Low" | Intensity "High" |
|---|---|---|
| A | 25.1 $\mu$W | — |
| B | 15.2 $\mu$W | 19.0 $\mu$W |
| C | 18.4 $\mu$W | 22.7 $\mu$W |
| D | 32.1 $\mu$W | 38.7 $\mu$W |

It was found that probe D could not be used to take measurements in practice, since the system became self-oscillating. This problem was not rectified. Probes B and C were found to provide a better result than probe A, probably because the light emitted had a longer wavelength (875 nm for probe A, 950 nm for probes B and C and 940 nm for probe D).

Measurements and Results

The auto-measuring process was effected by recording the PPG-signal on tape. The respiration frequency was also taped at the same time. When measuring blood circulation on human beings, the heart frequency was also measured, but with other methods. These signals were used as reference signals for the two components of the PPG-signal.

Measurements were taken on three different groups of objects, namely animals, infants in incubators, and adult males aged 35-years.

A narrow selection of the measurements taken are presented below. This selection is neither a random selection or a particularly representative selection. It is rather an example of those measurements which were considered to be of interest in evaluating the technique. An attempt to form a conclusion from these measuring processes is made below.

Measuring Equipment

In addition to the aforedescribed PPG-equipment, the respiration frequency of animals and adult human beings was measured with the aid of Strain Gauge equipment, which had the form of a strain sensor consisting of a thin rubber hose filled with mercury and connected to a measuring bridge. The heart frequency of the adult human beings was measured with the aid of laser-doppler equipment. When laser-doppler equipment was used, a minor investigation was also carried out in order to ascertain whether or not the respiration frequency could be traced in the laser-doppler signal. The heart frequency was not measured separately on the animals used in the experiment. In the case of infants, the heart frequency was measured with ECG and respiration was measured with an impedance plethysmograph.

The measured signals were coupled directly to a measurement tape-recorder and thereafter to an oscilloscope, where they could be monitored during the actual measuring process.

Processing Measurement Data

No measurement data was processed during the actual measuring processes. All data processing was, instead, carried out on the taped signals. The measurement data was processed in three different ways, namely by filtration, Fourier analysis and cross-correlation.

Filtration

The PPG-signal was coupled to a system of active filters, where different types of filter, limit frequencies and amplifications could be set. This enabled the different components to be filtered-out and compared with respective reference signals. The two signals were presented simultaneously on a printer.

Fourier Analysis

The signals were processed on an Ericsson PC, using the signal processing programme ASYSTANT. The power spectrum of the PPG-signals and the reference signals was calculated and comparisons subsequently made in the frequency plane.

Cross-Correlation

The cross-correlation function is a good way of ascertaining whether or not the periodicity of one signal is found in another signal. For example, it can be ascertained whether support is found for the assumption that the respiration period is found in the PPG-signal.

The cross-correlation function C(k) is calculated by the computer as:

$$C(k) = 1/N \sum_{n=0}^{N-1-|k|} X(n) \, Y(n + |k|)$$

where N is the number of measuring points, k is the shift between the signals, X(n) is the one signal and Y(n) is the other signal. It should be noted that the computer works with sampled signals.

The cross-correlation function is thus a form of convolution function where the one signal can be said to "slide" over the other. Assume, for example, that one signal is the PPG-signal and the other the respiration signal measured with a Strain Gauge. If the respiration frequency is found in the PPG-signal, there is obtained a periodic cross-correlation function which has the same periodicity as the respiration function. Furthermore, in this case, the functions are symmetrical and, when there is no time-shift between the signals, their maximum amplitude for k will be equal to 0, since the signals will then be superimposed and all values will be contributing.

Measurements on Adult Males

When taking these measurements, the PPG-probe holder was taped firmly to the skin of the patient. The Strain Gauge sensor was fastened over the thorax. The laser-dobbler probe was also secured with double-adhesive tape. The measurement object rested on a bed during the whole of the measuring process. Several measuring processes were carried out. The results obtained when measuring the blood circulation on a finger, the thorax and the forehead are given below.

Measuring Blood Circulation on a Finger

The finger tip is an extremely good region on which to measure blood circulation using PPG-technology. The signal is strong and has pronounced peaks or spikes for each heartbeat. The question asked prior to effecting this measuring process was whether or not it would be possible to detect respiration frequency. The PPG-probe C and low light intensity were used in this measuring process.

Studies in the time plane showed that the PPG-signal exhibited clear heart-signal peaks. A periodic low-frequency variation was also observed. The variation in amplitude between heartbeats was about 1 V, the maximum variation reaching to about 3 V. When counting the spikes or peaks in the two resultant diagrams, there is obtained a pulse of 54 beats per minute in both cases.

In a subsequent series of tests, the PPG-signal was filtered in a high-pass filter having a limit frequency of 0.5 Hz. The low-frequency variation was then filtered-out.

The PPG-signal was then passed through a low-pass filter having a limit frequency of 0.5 Hz. The respiration signal was used as a reference signal. Good agreement was found between the signals. The amplitude variations in the PPG-signal were about 3 V. When counting the peaks or spikes, a respiration frequency of 15 breaths per minute was obtained.

In a subsequent test series, the PPG-signal was passed through a low-pass filter having a limit frequency of 0.5 Hz and the test objects were asked to hold their breath. Variations in the PPG-signal were observed to fall and became smaller than 1 V.

Frequency Analysis

Since the test objects were at rest throughout the whole of the measuring process, it can be assumed that the signal was stationary over a long period of time. Consequently, frequency studies were carried out at measuring intervals of slightly longer than 50 seconds (1024 occasions). When studying the power spectrum of the PPG-signal and the power spectrum of the respiration signal and the laser-doppler signal, it was found that the PPG-signal contained two frequency peaks which coincided with the respiration peak and the heart-frequency peak.

Cross-Correlation

The cross-correlation function between the different measuring methods was calculated at intervals of 25 seconds. It was evident from this that the PPG-signal was well correlated with both the respiration and laser-doppler measurement values. The laser-doppler signal, on the other hand, was not particularly correlated with the respiration signal. The laser-doppler technique is thus not suited for measuring respiration frequency.

Conclusion

The finger tip is a splendid location in which to perform the PPG-technique. Both the respiration frequency and the heart frequency could be measured with the equipment used.

Thorax Measurement

A similar test series was carried out with the probe placed in the third intercostal space. Probe A with low light intensity was used in this instance.

Conclusion

The tests showed that the thorax is also a feasible region on which to take measurements in accordance with this technique. It is probable that thorax movements were reflected in the signal.

Forehead Measurement

The last measuring process carried out on adult human beings comprised a series of tests with the probe placed on the forehead of the object. Probe C with low intensity was used in this case. It was established that the forehead is not a good region on which to take measurements with the aid of PPG-technology, since the response is very weak. On the other hand, the forehead is a region which exhibits low-frequency variation of blood flow in the head, designated vasomotion. It is possible to detect this variation with laser-doppler technique. The investigation was intended to show whether or not this variation is discernible with PPG-technology or whether it is respiration that is measured.

Conclusion

A frequency study of the measuring results, and primarily of the cross-correlation function, showed clearly that the PPG-signal contained both respiration frequency and heart frequency. This is not seen clearly in the time-plane, however, which is possibly because the forehead is not a good region on which to carry out the measuring process. The laser-doppler signal also contained low-frequency components, as evident from the frequency spectrum. This is probably due to vasomotion. It is also possible that this variation is also found in the PPG-signal.

Measuring the Blood Circulation of Infants in Incubators

When measuring the blood circulation of infants, it was found that the respiration component was clearly dominating and not the heart frequency as in the case of the adult human beings. This can be explained by the fact that the thorax-configuration of infants produces a more pronounced thoracical subpressure when infants inspire. Furthermore, the heart frequency of infants is much higher than that of adult human beings, up to 200 beats per minute. The respiration frequency is also higher, namely up to 100 breaths per minute. The infants were monitored continuously with respect to heart frequency, which was registered by ECG, and respiration, which was registered by impedance plethysmography. The same electrodes were used for both measuring processes. The two measuring signals were taped simultaneously with the PPG-signal. The blood circulation of three different infants was measured in total.

Conclusion

The series of tests carried out showed that the technique also functions with infants, although respiration frequency is the dominant signal component in this case. It is far more difficult to filter out both of the components, since it is necessary to heavily suppress the strong respiration frequency. The limit frequency chosen for the high-pass filter lay close to the heart frequency, in order to be able to suppress the respiration frequency. The reason why the heart frequency was very weak and needed to be further amplified can be explained by the fact that the measuring process was carried out on the thorax and that thorax movement obviously contributed to the respiration component.

Additional Measuring Processes

A similar series of measuring processes was carried out on infants who lay on their stomachs with the probe fastened to the spines of respective infants and on the soles of the feet of said infants. The results showed that the respiration frequency was the dominant component even when measuring blood circulation at locations so widely spaced as the thorax and the soles of the feet. The amplitude of the PPG-signal obtained when measuring blood circulation in the soles of the feet was lower, however, than the amplitude obtained in the other measuring processes.

Measuring Blood Circulation on Animals

The blood circulation of ten dogs and two cats was measured. All animals were either given a general aesthetic or were locally anaesthetized before performing the different surgery entailed. The stomachs of many of the animals were shaved, in which case blood circulation was measured on the shaved part of the skin. The probe holder was attached to a rubber belt placed tightly around the animal concerned. Respiration was recorded with the aid of a Strain Gauge device. Heart frequency was not measured separately.

It was more difficult to analyze the measuring data obtained with animals than the measuring data obtained with human beings. The signal quality was poorer. As with the case when measuring the blood circulation of infants, it was found that the respiration frequency was the dominant component of the signal. The measuring results obtained with the various dogs differed radically. It was difficult to establish a pattern in the results obtained. Difficulties were also experienced in filtering-out the two components. The heart frequency was especially difficult to find. A heart-frequency reference signal was often desired. Neither did the frequency analysis provide a clear result. The spectrum contained many peaks whose origins were difficult to establish. A great deal of this uncertainty is probably due to harmonics. Neither do dogs always have a uniform heart frequency, since the heart frequency of dogs is influenced by respiration, among other things. As a result, the signal is not stationary for any length of time, which makes frequency analysis difficult.

Evaluation of the Measuring Results

The series of tests carried out indicate that it is quite possible to detect the respiration frequency and heart frequency of adult human beings and infants with the aid of equipment constructed in accordance with the present invention. With regard to measuring the blood circulation of animals, the results are more dubious.

Several of the measuring processes, however, showed positive tendencies and it is probably also possible to measure the blood circulation of animals, although it is necessary to improve signal quality in this case.

An Attempt to Quantify the Measuring Results

The following table summarizes the measuring processes carried out and constitutes an attempt to quantify the quality of the measurements on the processed signals and calculated signal parameters. This assessment is objective and the values presented in the table have the following vague significance:

3 A very good and clear signal or signal parameter, which should suffice for some form of electronic detection process.

2 A relatively clear signal or signal parameter to the eye of a human being, although not suitable for electronic detection unless processed.

1 A very unclear signal or signal parameter, although capable of being discerned by the trained eye. Not suitable for electronic detection.

0 The component sought cannot be discerned in the signal or the signal parameter.

— No measuring process was carried out.

The mean value of the assessment made for each measuring process is given in the table. This measurement is an extremely rough measurement and should only be used to obtain a general idea of the assessments carried out.

sary to separate from the detected PPG-signal that signal component which indicates the respiration frequency of the object.

The presentation unit may vary in accordance with requirements, and may be a display or printer, for instance.

The filter used is preferably a digital filter.

The filter or filters is/are provided with means for adjusting limit frequencies and degrees of amplification. The filter or filters is/are preferably adapted to detect the frequency content of the PPG-signal electronically for selection and setting of suitable limit frequencies.

In order to obtain a reliable monitoring apparatus, the apparatus should also include a microprocessor which is programmed to calculate the Fourier transform. A microprocessor of this kind may also be programmed to separate signals relating to the heart frequency and respiration frequency of the object by digital filtration. The microprocessor may also be programmed to eliminate disturbances, for example disturbances emanating from stray light having a frequency of 50 Hz.

Figure 6:
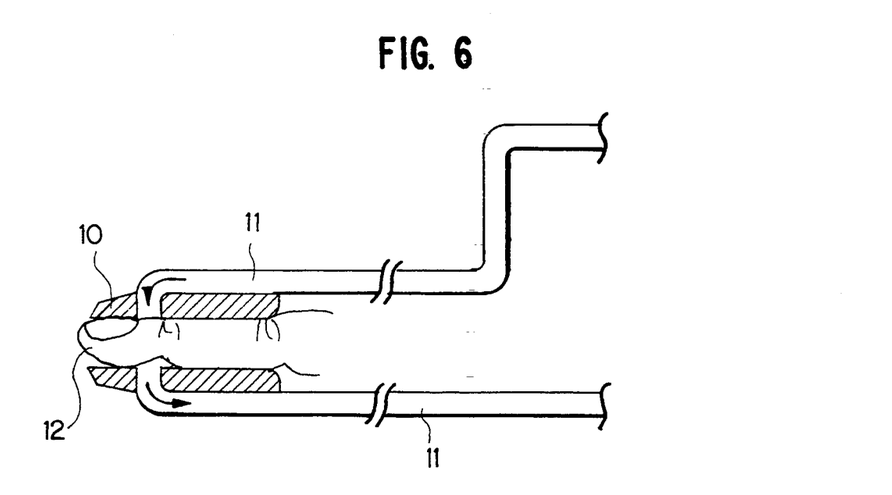
FIG. 6 illustrates the principle of transmission measuring with the aid of fibre optics and with the aid of a probe fitted to one finger of the object.

FIG. 6 illustrates a modified embodiment in which a probe 10 coacts with fibre optics and is placed on a finger 12. When light is passed through the optical fibres 11, there is obtained a system which is resistant to electromagnetic disturbances, a facility which is extremely important within health care organizations.

The apparatus illustrated in FIG. 6 enables heart and respiration frequencies to be recorded while performing surgery with diathermy, which was not previously pos-

TABLE 3

|  | Unprocessed signal | | Filtered signal | | Frequency analysis | | Cross-corr. | | |
| --- | --- | --- | --- | --- | --- | --- | --- | --- | --- |
|  | Heart. | Resp. | Heart. | Resp. | Heart. | Resp. | Heart. | Resp | Mean value |
| Adult | | | | | | | | | |
| Finger | 3 | 1 | 3 | 3 | 3 | 3 | 3 | 3 | 2.8 |
| Thorax | 2 | 1 | 3 | 3 | 3 | 3 | 2 | 2 | 2.5 |
| Forehead | 3 | 0 | - | 2 | 3 | 3 | 3 | 3 | 2.4 |
| Infants | | | | | | | | | |
| Thorax | 0 | 3 | 3 | 3 | 3 | 3 | 2 | 3 | 2.5 |
| Spine | 0 | 2 | 2 | 3 | 2 | 2 | 1 | 3 | 1.9 |
| foot sole | 0 | 2 | 3 | 3 | 3 | 2 | 2 | 2 | 2.1 |
| Animals | | | | | | | | | |
| Spaniel | | | | | | | | | |
| Stomach | 0 | 3 | 2 | — | 0 | 2 | — | 2 | 1.3 |
| Rear leg | 0 | 3 | 2 | — | 0 | 3 | — | 3 | 1.8 |
| Terrier | | | | | | | | | |
| Stomach | 1 | 1 | 2 | 3 | 0 | 3 | — | 3 | 1.9 |
| Spine | 1 | 0 | 1 | 0 | 0 | 0 | — | 0 | 0.3 |
| Cat | | | | | | | | | |
| Stomach | 0 | 3 | 2 | — | 0 | 3 | — | 3 | 1.8 |
| Back paw | 0 | 0 | 2 | 2 | 0 | 3 | — | 3 | 1.4 |

By unprocessed signal is meant a low-pass filtered signal having the limit frequency 5 or 10 Hz.

Apparatus for Measuring Blood Circulation Directly on a Object

On the basis of the test series briefly described above, there has been developed an apparatus which enables blood circulation to be measured directly on a object such as a human being or an animal. This apparatus, which is of the kind defined in claim 1, enables the heart frequency and respiration frequency of a patient, or object, to be monitored continuously on a display or by means of a printer.

The probe used with the apparatus includes a light source, a detector unit and an electronic amplifier unit and may be of the kind described above. The apparatus may also include the aforedescribed filter units necessible.

The presentation unit used with the inventive monitoring apparatus shall be constructed to correspond to the monitoring situation concerned. The unit should include the possibility of storing data over long periods of time, coupled with the possibility of quickly analyzing both the respiration frequency and heart frequency. The unit should also include conventional alarm functions, for example bradycardia and tachycardia alarm functions respectively, and also a respiration-state alarm function. The unit should also provide the possibility of documenting other media, i.e. printed media for medical journal or case history entries.

The monitoring unit may also include other, purposeful functions, for example a function which enables automatic adjustment of different signal amplitudes of the respiration and heart activities of different patients and at different medical states or conditions. The alarm-signalling part of the unit which includes the relevant alarm limits will preferably be capable of modification in accordance with prevailing circumstances.

It will be evident from the aforegoing that the inventive monitoring apparatus which enables both the respiration frequency and heart frequency to be measured simultaneously in a disturbance-free and galvanically-insulated fashion has a number of interesting applications in a plurality of situations where present-day methods and apparatus become disturbed or are dangerous to use. Examples of such applications include monitoring of a patient during surgery in which diathermy is applied, monitoring in high electric and magnetic fields, for instance during MR-investigations, and working-physiological investigations in industrial environments. The inventive monitoring apparatus can also be used advantageously, for example, in combination with other methods, such as pulsoxymetry, where it is desirable to record heart frequency, respiration frequency and oxygen-gas saturation, and also defibrillation with the aid of a probe.

The inventive monitoring apparatus can also be used in special investigations or examinations, for example in a magnetic camera while crushing kidney stones, and also in irradiation processes where other methods become disturbed.

The monitoring apparatus can also be used in veterinary medicine, particularly for assessing the depth of anaesthesis during surgery.

Other applications in which present-day methods are difficult to apply because of electromagnetic or acoustic disturbances include, for example, working-physiological evaluations, studies in heavy industry, the physiological reactions of fighter pilots under flying conditions, etc.

We claim:

1. A monitoring apparatus for analyzing a frequency of a pulse obtained by measuring blood circulation of a subject photoplethysmographically, said apparatus comprising:
   a) a light source for emitting a light beam toward a surface of said subject,
   b) a detector unit for detecting a photoplethysmographic (PPG) signal, generated by said light beam and including an AC-component which represents a heart frequency of said subject,
   c) an electronic amplifying unit for amplifying said detected PPG-signal and outputting an amplified PPG-signal,
   d) means for separating from said amplified PPG-signal an amplified signal component representing a component of said detected PPG-signal which indicates a respiration frequency of said subject, and
   e) means for determining the respiration frequency of said subject based on said amplified signal component.

2. An apparatus according to claim 1, wherein said component separated by said separating means represents variations in blood flow in skin of said subject caused by the respiration frequency of said subject.

3. An apparatus according to claim 1, further comprising at least one filter means for setting limit frequencies and degrees of amplification of said amplified PPG-signal.

4. An apparatus according to claim 3, further comprising means for electronically detecting frequencies of said amplified PPG-signal to enable said filter means to set said limit frequencies.

5. An apparatus according to claim 4, wherein said filter means adjust in accordance with at least one of said heart and respiration frequencies to set said limit frequencies.

6. An apparatus according to claim 1, further comprising means for compensating for a DC component of said detected PPG-signal to reduce energy loss of said detected PPG-signal due to low-frequency components of said detected PPG-signal.

7. An apparatus according to claim 1, further comprising a probe which includes means for directing said light beam to said surface of said subject and means for capturing a portion of said light beam which passes through said subject or is reflected thereby and directing said portion of said light beam to the detector unit.

8. An apparatus according to claim 7, wherein said directing means and said capturing and directing means each comprise optical fibers.

9. An apparatus according to claim 1, further comprising a microprocessor for at least one of calculating a Fourier transform of said amplified PPG-signal and digitally filtering said amplified PPG-signal to separate said components representing the heart frequency or respiration frequency of said subject from said amplified PPG-signal.

10. A method of measuring blood circulation of a subject photoplethysmographically by using a light source, a detector unit for detecting a generated PPG-signal including an AC-component representing a heart frequency of the subject, an electronic amplifying unit and a presentation unit, comprising the steps of:
   separating from the detected PPG-signal a signal component indicating a respiration frequency of the object; and
   determining the respiration frequency of the subject based on said signal component.

11. A method according to claim 10, wherein said signal component represents variations in blood circulation within the skin of said subject caused by the respiration frequency of said subject.

* * * * *